United States Patent [19]
Grinnell et al.

[11] Patent Number: 6,156,734
[45] Date of Patent: *Dec. 5, 2000

[54] METHODS FOR TREATING HYPERCOAGULABLE STATES OR ACQUIRED PROTEIN C DEFICIENCY

[75] Inventors: Brian William Grinnell; Daniel Lawrence Hartman; Sau-Chi Betty Yan, all of Indianapolis, Ind.

[73] Assignee: Eli Lilly and Company, Indianapolis, Ind.

[ * ] Notice: This patent is subject to a terminal disclaimer.

[21] Appl. No.: 09/415,876

[22] Filed: Oct. 8, 1999

Related U.S. Application Data

[63] Continuation of application No. 09/174,507, Oct. 16, 1998, Pat. No. 6,008,199.
[60] Provisional application No. 60/062,549, Oct. 20, 1997, and provisional application No. 60/064,765, Nov. 7, 1997.

[51] Int. Cl.[7] .......................... A61K 38/00; A61K 38/01; A61K 38/02
[52] U.S. Cl. .................. 514/21; 514/2; 514/12; 514/802; 424/701; 424/372; 435/219; 435/226; 530/381; 530/382; 530/383; 530/384; 530/385; 530/386
[58] Field of Search ................... 514/2, 12, 21, 514/802; 424/101, 372; 435/219, 226; 530/380, 381, 382, 383, 384, 385, 386

[56] References Cited

U.S. PATENT DOCUMENTS

| | | | |
|---|---|---|---|
| 4,775,624 | 10/1988 | Bang et al. | 435/226 |
| 4,981,952 | 1/1991 | Yan | 530/384 |
| 4,992,373 | 2/1991 | Bang et al. | 435/226 |
| 5,009,889 | 4/1991 | Taylor, Jr. et al. | 514/2 |
| 5,453,373 | 9/1995 | Gerlitz et al. | 435/240.2 |
| 5,478,558 | 12/1995 | Eibl et al. | 424/94.63 |
| 5,516,650 | 5/1996 | Foster et al. | 435/68.1 |
| 6,008,199 | 12/1999 | Grinnell et al. | 514/21 |

FOREIGN PATENT DOCUMENTS

| | | |
|---|---|---|
| 0 445 939 | 9/1991 | European Pat. Off. . |
| 7097335A | 4/1995 | Japan . |
| 8325161A | 12/1996 | Japan . |
| WO 97/20043 | 6/1997 | WIPO . |

OTHER PUBLICATIONS

Mesters, et al., "Factor VIIa and Antithrombin III Activity During Severe Sepsis and Septic Shock in Neutropenic Patients", *Blood* 88: 881–886, 1996.
Fourrier, et al., "Septic Shock, Multiple Organ Failure, and Disseminated Intravascular Coagulation", *Chest* 101:816–823, 1992.
Taylor, et al., "Protein C Prevents the Coagulopathic and Lethal Effects of *Escherichia coli* Infusion in the Baboon", *J. Clin. Invest.* 79:918–925, 1987.
Murakami, et al. "Activated Protein C Attenuates Endotoxin–Induced Pulmonary Vascular Injury by Inhibiting Activated Leukocytes in Rats", *Blood* 87:642–647, 1996.

Okamoto, et al., "Protective Effect of Neutrophil Elastase Inhibitor (EI) and Activated Protein C (APC) on the Organ Failure and Coagulopathy in Cecal Ligation and Puncture (CLP) Sepsis in the Rabbit", *Gastroenterology* 106:A747, 1994.
"Anti–Inflammatory Therapies to Treat Sepsis and Septic Shock: A Reassessment", *Crit. Care Med.* 25:1095–1100, 1997.
Natanson, et al., "Selected Treatment Strategies for Septic Shock Based on Proposed Mechanisms of Pathogenesis", *Ann. Intern. Med.* 120(9):771–783, 1994.
Gibaldi, "Anatomy of an Antibody, and Related Misadventures in Developing an Effective Treatment for Septic Shock", *Pharmacotherapy* 13(4) :302–308, 1993.
Parrillo, "Pathogenetic Mechanisms of Septic Shock", *N. Engl. J. Med.* 328(20):1471–1477, 1993.
Levi, et al., "Pathogenesis of Disseminated Intravascular Coagulation in Sepsis", *JAMA* 270:975–979, 1993.
Esmon, "The Protein C Anticoagulant Pathway", *Arteriosclerosis & Thromb.* 12:135–145, 1992.
Taylor, et al., "DEGR–Factor Xa Blocks Disseminated Intravascular Coagulation Initiated by *Escherichia coli* without Preventing Shock or Organ Damage", *Blood* 78:362–368, 1991.
Maraganore, "Hirudin and Hirulog™: Advances in Antithrombotic Therapy", *Perspective in Drug Discovery and Design* 1:461–478, 1994.
Gerson, et al., "Severe Acquired Protein C Deficiency in Purpura Fulminans Associated with Disseminated Intravascular Coagulation: Treatment with Protein C Concentrate", *Pediatrics* 91(2):418–422, 1993.
Smith, et al., "Successful Treatment of Meningoccal Induced Protein C Deficiency/Purpura Fulminans in Children with Protein C Concentrate and Heparin", *Thromb. Haemost*, PS1709, p. 419, 1997.
Rintala, et al., "Protein C in the Treatment of Coagulopathy in Meningococcal Disease", *Lancet* 347:1767, 1996.
Rivard, et al., "Treatment of Purpura Fulminans in Meningococcemia with Protein C Concentrate", *J. Pediatr.* 126:646–652, 1995.
Smith, et al., "Use of Protein–C Concentrate, Heparin, and Haemodiafiltration in Meningococcus–Induced Purpura Fulminans", *The Lancet* 350:1590–1593, 1997.
Veldman, et al., "Treatment of DIC in Septic Shock with Protein C Concentrate", *Blood* 90:3271, 1997.
Powars, et al., "Epidemic Meningococcemia and Purpura Fulminans with Induced Protein C Deficiency", *Clin. Infectious Diseases* 17:254–261, 1993.

(List continued on next page.)

*Primary Examiner*—F. T. Moezie
*Attorney, Agent, or Firm*—Brian P. Barrett; Steve Caltrider

[57] ABSTRACT

A method of treatment for human patients with an acquired hypercoagulable state or acquired protein C deficiency associated with sepsis, purpura fulminans, meningococcal sepsis, bone marrow and other transplantations, severe burns, pregnancy, major surgery, severe trauma, or ARDS, which comprises administering activated protein C providing a highly selective therapeutic agent with a low potential for causing bleeding complications.

30 Claims, No Drawings

OTHER PUBLICATIONS

Haire, et al., "Multiple Organ Dysfunction Syndrome in Bone Marrow Transplantation", *JAMA* 274:1289–1295, 1995.

Harper, et al., "Protein C Deficiency and Portal Thrombosis in Liver Transplantation in Children", *Lancet* 924–927, 1988.

Sorenson, et al., "Protein C in Renal Aliotransplantation During the Perioperative Period", *J. Inter. Med.* 226:101–105, 1989.

Gordon, et al;, "Thrombotic Complications of BMT: Association with Protein C Deficiency", *Bone Marrow Transplan.* 11:61–65, 1993.

Bazarbachi, et al., "Changes in Protein C, Factor VII and Endothelial Markers After Autologous Bone Marrow Transplantation: Possible Implications in the Pathogenesis of Veno–Occlusive Disease", *Nouv Rev Fr Hematol* 35:135–140, 1993.

Paioni, et al., "Naturally Occurring Anticoagulants and Bone Marrow Transplantation: Plasma Protein C Predicts the Development of Venocclusive Disease of the Liver", *Blood* 81:3458–3462, 1993.

Collins, et al., "Factor VIIa and Other Haemostatic Variables Following Bone Marrow Transplantation", *Thromb. And Haemo.* 72:28–32, 1994.

Harper, et al., "Changes in the Natural Anticoagulants Following Bone Marrow Transplantation", *Bone Marrow Trans.* 5:39–42, 1990.

Veldman, et al., "A New Option in the Treatment of VOD After BMT: Continuous Infusion of Recombinant Tissue Plasminogen Activator and Protein C", *Bone Marrow Trans.* 21:S238, 1998.

Curreri, et al., "Coagulation Dynamics Following Thermal Injury", *Ann. Surg.* 181:161–163, 1974.

McManus, et al., "Disseminated Intravascular Coagulation in Burned Patients", *J. of Trauma* 13(5):416–422, 1973.

Lo, et al., "Protein C and Protein S Levels in Some Burn Patients", *Burns* 20:186–187, 1994.

Barbour et al., "Controversies in Thromboembolic Disease During Pregnancy: A Critical Review", *Obstet. Gynecol.* 86(4):621–633, 1995.

Dahlback, et al., "Inherited Thrombophilia: Resistance to Activated Protein C as a Pathogenic Factor of Venous Thromboembolism", *Blood* 85:607–614, 1995.

Conrad, et al., "Thrombosis and Pregnancy in Congenital Deficiencies in AT III, Protein C or Protein S: Study of 78 Women", *Throm. Haemost.* 63:319–320, 1990.

Perry, et al., "Abnormal Hemostasis and Coagulopathy in Preeclampsia and Eclampsia", *Clin. Obstet. Gynecol.* 35:338–350, 1992.

Uzan, et al., "Elements de Physiopathologie de la Pre–Eclampsie et Place des Principaux Examens Complementaires", *Rev Fr Gynecol. Obstet.* 86:158–163, 1991.

Rathgeber, et al., "Anasthesiologische und Intensivmedizinische Aspekte der Schweren Praeklampsie Mit HELLP–Syndrom", *Anasth Intensivther Notfallmed* 25:206–211, 1990.

De Stefano, et al., "Thrombotic Risk during Pregnancy and Puerperium in Women with APC–Resistance—Effective Subcutaneous Heparin Prophylaxis in a Pregnant Patient", *Thromb Haemost* 74:793–794, 1995.

Watkins, et al., "The Early Diagnosis of Impending Coagulopathies Following Surgery and Multiple Trauma", *Klin Worchenschr* 63:1019–1027, 1985.

Thomas, et al., "Primary Hypercoagulable States in General and Vascular Surgery", *Am. J. Surgery* 158:491–494, 1989.

LeClerc, J. R., "Low–Molecular Weight Heparin Prophylaxis in Surgical Patients", *Clin. Appl. Thrombosis/Hemostasis* 3(3):153–156, 1997.

Collins, et al., "Pitfalls in Peripheral Vascular Surgery: Disseminated Intravascular Coagulation", *Am. J. Surgery* 124:375–380, 1977.

Menges, et al., "The Role of the Protein C–Thrombomodulin System and Fibrinolysis During Cardiovascular Surgery: Influence of Acute Preoperative Plasmapheresis", *J. Cardiothor Vasc An.* 10:482–489, 1996.

Mayer, et al., "Coagulopathies Associated With Major Spinal Surgery", *Clin. Orthop.* 245:83–89, 1989.

Blamey, et al, "Protein C Antigen Levels in Major Abdominal Surgery: Relationships to Deep Vein Thrombosis, Malignancy and Treatment with Stanozolol", *Thromb. Haemost.* 54:622–625, 1985.

Grinnell, et al., "Trans–Activated Expression of Fully Gamma–Carboxylated Recombinant Human Protein C, An Antithrombotic Factor", *Bio/Technology* 5:1189–1192, 1987.

Graybill, et al., "Complement and Coagulation in Rocky Mountain Spotted Fever", *Southern Medical Journal*, 66(4):414–413, 1973.

Loubser, et al., "Severe Illness caused by *Rickettsia conorii*", *Annals of Tropical Paediatrics* 13:277–280, 1993.

Koul, et al., "Haemostatic Abnormalities in Multidrug–Resistant Enteric Fever", *Acta Haematol* 93:13–19, 1995.

Carpenter, et al., "Purpura Fulminans in Pneumococcal Sepsis: Case Report and Review", *Scand J Infect Dis* 29:479–483, 1997.

Butler, et al., "*Yersinia pestis* Infection in Vietnam. I. Clinical and Hematologic Aspects", *The Journal of Infectious Disease* 129:578–584, 1974.

Lercari, et al., "Apheresis for Severe Malaria Complicated by Cerebral Malaria, Acute Respiratory Distress Syndrome, Acute Renal Failure, and Disseminated Intravascular Coagulation", *Journal of Clinical Apheresis* 7:93–96, 1992.

Puthucheary, et al., "Septicaemic melioidosis: a review of 50 cases from Malaysia", *Transactions of the Royal Society of Tropical Medicine and Hygiene* 86:683–685, 1992.

Ota, "Successful Treatment of Severe Odontogenic Infections which caused Septicemia", Y., *J. Japanese Assoc. Infec. Dis.* 68:157–161, 1994.

Nguyen, et al., "Varicella and thrombotic complications associated with transient protein C and protein S deficiencies in children", *Eur J Pediatr* 153:646–649, 1994.

Franz, et al., "Clinical Recognition and Management of Patients Exposed to Biological Warfare Agents", *Journal of the American Medical Assoc.* 278(5):399–411, 1997.

Hill, et al., "Leptospiral Pneumonia", *Seminars in Respiratory Infections* 12(1):44–49, 1997.

Levin, "Syndromes with Renal Failure and Shock", *Pediatric Nephrology* 8:223–229, 1994.

Deyama, et al., *Nippon Geka Gakki Zasshi* 92:907–12, 1991.

Okajima, et al., "Treatment of Patients with Disseminated Intravascular Coagulation by Protein C", *Amer. J. of Hematology* 33:277–278, 1990.

Howey, et al., "Preparation for Trials of Recombinant Activated Protein C in Sepsis: A Pharmacokinetic and Dynamic Study in Healthy Men and Women", *Chest* 112(3): 898, 1997.

METHODS FOR TREATING HYPERCOAGULABLE STATES OR ACQUIRED PROTEIN C DEFICIENCY

PRIORITY

This application is a Continuation of U.S. patent application Ser. No. 09/174507, filed Oct. 16, 1998 now U.S. Pat. No. 6,008,199, which claimed the benefit of U.S. Provisional Applications Nos. 60/062,549 filed Oct. 20, 1997, now abandoned, and 60/064,765 filed Nov. 7, 1997, now abandoned.

FIELD OF THE INVENTION

This invention relates to medical science particularly the treatment of hypercoagulable states or acquired protein C deficiency with activated protein C.

BACKGROUND OF THE INVENTION

Protein C is a serine protease and naturally occurring anticoagulant that plays a role in the regulation of hemostasis through its ability to block the generation of thrombin production by inactivating Factors Va and VIIIa in the coagulation cascade. Human protein C is made in vivo primarily in the liver as a single polypeptide of 461 amino acids. This precursor molecule undergoes multiple post-translational modifications including 1) cleavage of a 42 amino acid signal sequence; 2) proteolytic removal from the one chain zymogen of the lysine residue at position 155 and the arginine residue at position 156 to make the 2-chain form of the molecule, (i.e., a light chain of 155 amino acid residues attached through a disulfide bridge to the serine protease-containing heavy chain of 262 amino acid residues); 3) vitamin K-dependent carboxylation of nine glutamic acid residues clustered in the first 42 amino acids of the light chain, resulting in 9 gamma-carboxyglutamic acid residues; and 4) carbohydrate attachment at four sites (one in the light chain and three in the heavy chain). The heavy chain contains the well established serine protease triad of Asp 257, His 211 and Ser 360. Finally, the circulating 2-chain zymogen is activated in vivo by thrombin at a phospholipid surface in the presence of calcium ion. Activation results from removal of a dodecapeptide at the N-terminus of the heavy chain, producing activated protein C (aPC) possessing enzymatic activity.

In conjunction with other proteins, aPC functions as perhaps the most important down-regulator of blood coagulation resulting in protection against thrombosis. In addition to its anti-coagulation functions, aPC has anti-inflammatory effects through its inhibition of cytokine generation (e.g. TNF and IL-1) and also exerts profibrinolytic properties that facilitate clot lysis. Thus, the protein C enzyme system represents a major physiological mechanism of anti-coagulation, anti-inflammation, and fibrinolysis.

SEPSIS

Sepsis is defined as a systemic inflammatory response to infection, associated with and mediated by the activation of a number of host defense mechanisms including the cytokine network, leukocytes, and the complement and coagulation/fibrinolysis systems. [Mesters, et al., *Blood* 88:881–886, 1996]. Disseminated intravascular coagulation [DIC], with widespread deposition of fibrin in the microvasculature of various organs, is an early manifestation of sepsis/septic shock. DIC is an important mediator in the development of the multiple organ failure syndrome and contributes to the poor prognosis of patients with septic shock. [Fourrier, et al., *Chest* 101:816–823, 1992].

Several encouraging pre-clinical studies using protein C in various animal models of sepsis have been reported. A study in a baboon sepsis model by Taylor, et al., [*J. Clin. Invest.* 79:918–25, 1987], used plasma-derived human activated protein C. The animals were treated prophylactically (i.e., the aPC was given at the start of the two hour infusion of the $LD_{100}$ *E. coli*). Five out of five animals survived 7 days and were considered permanent survivors to the experimental protocol. In control animals receiving an identical infusion of *E. coli*, five out of five animals died in 24 to 32 hours. The efficacious dose was 7 to 8 mg/kg.

In a lipopolysaccharide (LPS; *E. coli*) sepsis model in rats [Murakami, et al., *Blood* 87:642–647, 1996], the pulmonary vascular injury induced by LPS was inhibited by human plasma derived activated protein C at a dose of 100 $\mu$g/kg. Furthermore, in a ligation and puncture sepsis model in rabbits, Okamoto, et al., [*Gastroenterology* 106:A747, 1994], demonstrated that plasma derived human activated protein C was effective in protecting the animals from coagulopathy and organ failure at a dose of 12 $\mu$g/kg/hr for nine hours. Due to the species specificity of aPC, results obtained in these animals are not necessarily predictive to the treatment of humans. The efficacious dose level of human activated protein C is extremely variable and unpredictable depending upon the animal model selected. For example, the serum half-life of human activated protein C in humans is 30 to 40 minutes, compared to a half-life of 8 to 10 minutes in baboons and 90 minutes in rabbits.

There have been numerous recent attempts to treat sepsis in humans, for the most part using agents that block inflammatory mediators associated with the pathophysiology of this disease. However, clinical studies with a variety of agents that block inflammatory mediators have been unsuccessful [reviewed in Natanson, et al., *Ann. Intern. Med* 120:771–783, 1994; Gibaldi, *Pharmacotherapy* 13:302–308, 1993]. Since many of the mediators involved in inflammation are compensatory responses, and therefore have salutary effects, some investigators have suggested that blocking their action may not be appropriate [e.g., Parrillo, *N. Engl. J. Med.* 328:1471–1477, 1993].

Recently, blocking DIC has been proposed as a new target for clinical trials in sepsis [e.g., Levi, et al., *JAMA* 270:975–979, 1993]. However, simply blocking the coagulation defect in sepsis may not be sufficient. As reviewed by Esmon, [*Arteriosclerosis & Thromb.* 12:135–145, 1992], several antithrombotics have not shown efficacy in the baboon sepsis model, including active site-blocked factor Xa [Taylor, et al., *Blood* 78:364–368, 1991], hirudin and hirulog [Maraganore, *Perspective in Drug Discovery and Design* 1:461–478, 1994]. Each of these antithrombotics were able to block the consumptive coagulopathy in the animals but were not able to improve survival. Additionally, investigators in Japan [patent application JP7097335A] have proposed treating coagulopathy associated with hepatic insufficiency, which has the potential of developing DIC-like symptoms, with plasma derived activated protein C.

To date, plasma-derived human protein C zymogen has been used as a successful adjunct to aggressive conventional therapy in the management of twenty-five patients with purpura fulminans in bacterial sepsis of which twenty-two survived (Gerson, et al., *Pediatrics* 91:418–422, 1993; Smith, et al., *Thromb. Haemost*, PS1709, p419, 1997; Rintala, et al., *Lancet* 347:1767, 1996; Rivard, et al., *J. Pediatr.* 126:646–652, 1995). Gerson, et al., [1993] describe a case study of a treatment of a child with proven gram positive bacteremia and purpura fulminans, who was failing to respond to aggressive conventional treatment. The patient was treated with plasma-derived human protein C zymogen (280 µg/kg bolus+40 µg/kg/hr infusion) resulting in an associated correction of coagulopathy and DIC, and arrest of clinical signs of the development of septic shock-related purpura fulminans. Rintala, et al., [1996] reported the treatment of 2 adults with meningococcal septicemia presented with purpura fulminans. The patients were treated with plasma derived protein C zymogen at 400 µg/kg bolus every six hours for 8–10 days. One died and one survived. Rivard, et al., [1995] reported the treatment of four patients with meningococcemia presented also with purpura fulminans, who all survived following human protein C zymogen therapy. These patients were treated at a dose of 400 µg/kg bolus every six hours. Although the sample size from these studies is small, the mortality associated with meningococcemia presented with purpura fulminans is greater than 50% [Powars, et al., *Clin. Infectious Diseases* 17:254–261, 1993]. However, because these studies are conducted with human protein C zymogen, they offer little suggestion for establishing the dose and duration of therapy with activated protein C.

In addition to meningococcemia, purpura fulminans and/or DIC have been associated with numerous bacterial, viral, or protozoan infections which include but are not limited to infections caused by Rickettsia (Rocky Mountain Spotted fever, tick bite fever, typhus, etc.) [Graybill, et al., *Southern Medical Journal*, 66(4):410–413, 1973; Loubser, et al., *Annals of Tropical Paediatrics* 13:277–280, 1993]; Salmonella (typhoid fever, rat bite fever) [Koul, et al., *Acta Haematol*, 93:13–19, 1995]; Pneumococci [Carpenter, et al., *Scand J Infect Dis*, 29:479–483, 1997] *Yersina pestis* (Bubonic plague) [Butler et al., *The Journal of Infectious Disease*, 129:578–584, 1974]; *Legionella pneumophila* (Legionaires Disease); *Plasmodium falciparum* (cerebral malaria) [Lercari, et al., *Journal of Clinical Apheresis*, 7:93–96, 1992]; *Burkholderia pseudomallei* (Melioidosis); *Pseudomonas pseudomallei* (Melioidosis) [Puthucheary, et al., *Transactions of the Royal Society of Tropical Medicine and Hygiene*, 86:683–685, 1992]; Streptococci (Odontogenic infections) [Ota, Y., *J. Japanese Assoc. Infect. Dis.*, 68:157–161]; zoster virus [Nguyen, et al., *Eur J Pediatr*, 153:646–649, 1994]; *Bacillus anthracis* (Anthrax) [Franz, et al., *Journal of the American Medical Assoc.*, 278(5):399–411, 1997]; *Leptospira interrogans* (leptospirosis) [Hill, et al., *Seminars in Respiratory Infections*, 12(1):44–49, 1997]; Staphylococci [Levin, M., *Pediatric Nephrology*, 8:223–229]; *Haemophilus aegyptius* (Brazilian purpuric fever); Neisseria (gonococcemia, meningococcemia); and *mycobacterium tuberculosis* (miliary tuberculosis).

Even though the purpura fulminans, DIC or acquired protein C deficiency conditions in sepsis/septic shock or other infections have been well documented as indicated above, there is little data as to how to treat these patients with activated protein C. Establishing human dose levels using the pre-clinical pharmacology data generated from treatment with activated human protein C in animal models is difficult due to the species specificity properties of the biological actions of protein C.

TRANSPLANTATION

A variety of transplantation associated thromboembolic complications may occur following bone marrow transplantation (BMT), liver, kidney, or other organ transplantations [Haire, et al., *JAMA* 274:1289–1295, (1995); Harper, et al., *Lancet* 924–927 (1988); and Sorensen, et al., *J. Inter. Med* 226:101–105 (1989); Gordon, et al., *Bone Marrow Transplan.* 11:61–65, (1993)]. Decreased levels of circulating protein C have been reported after BMT [Bazarbachi, et al., *Nouv Rev Fr Hematol* 35:135–140 (1993); Gordon, et al., *Bone Marrow Trans.* 11:61–65 (1993)], renal transplantation [Sorensen, et al., *J. Inter. Med* 226:101–105 (1989)], and liver transplantation [Harper, et al., *Lancet* 924–927(1988)]. This deficiency in protein C contributes to a hypercoagulable state placing patients at risk for thromboembolic complications.

For example, hepatic venocclusive disease (VOD) of the liver is the major dose-limiting complication of pretransplantation regimens for BMT. VOD is presumably the result of small intrahepatic venule obliteration due to intravascular deposition of fibrin. [Faioni, et al., *Blood* 81:3458–3462 (1993)]. In addition, VOD causes considerable morbidity and mortality following BMT [Collins, et al., *Throm. and Haemo.* 72:28–33 (1994)]. A decreased level of protein C coincident with the peak incidence of VOD has been reported [Harper, et al., *Bone Marrow Trans.* 5:39–42 (1990)] and is likely to be a contributing factor to the genesis of this condition Organ dysfunction after BMT including pulmonary, central nervous system, hepatic or renal, is a complication that occurs in a high percentage of transplant patients [Haire, et al., *JAMA* 274:1289–1295, (1995)]. A single organ dysfunction in BMT is a strong predictor of multiple organ dysfunction syndrome (MODS) which is the leading cause of death in BMT patients. Disseminated intravascular coagulation (DIC) due to a massive activation of the coagulation system and widespread deposition of fibrin in the microvasculature of various organs is an important mediator in the development of MODS [Fourrier, et al., *Chest* 101:816–823 (1992)]. Thus, a deficiency in protein C levels in patients who have undergone bone marrow or other organ transplantations leads to a hypercoagulable state that predisposes the patients to venous thromboembolic complications and organ dysfunction. A need currently exists to determine a method of treating humans with a hypercoagulable state associated with organ transplantations utilizing activated protein C.

BURNS

It has long been recognized that severely burned patients have complications associated with hypercoagulation [Curreri, et al., *Ann. Surg.* 181:161–163 (1974)]. Burned patients have supranormal in vitro clotting activity and frequently develop DIC which is characterized by the sudden onset of diffuse hemorrhage; the consumption of fibrinogen, platelets, and Factor VIII activity; intravascular hemolysis; secondary fibrinolysis; and biopsy evidence of microthrombi [McManis, et al., *J. of Trauma* 13:416–422, (1973)]. Recently, it was reported that the levels of protein C were reduced drastically in severely burned patients and that this reduction of the natural anticoagulant may lead to an increase in the risk of DIC [Lo, et al., *Burns* 20:186–187 (1994)]. In addition, Ueyama, et al., in discussing the pathogenesis of DIC in the early stage of burn injury, concluded that massive thrombin generation and decrease of anticoagulant activity may occur in proportion to the severity of burns [Ueyama, et al., *Nippon Geka Gakkai Zasshi* 92:907–12 (1991)]. DIC is one of the common complications in patients suffering from severe burn injuries.

Protein C deficiency has been documented in severely burned patients as indicated above, however, there is little data regarding whether protein C replacement therapy would be effective or regarding how to treat these patients with activated protein C.

PREGNANCY

It is well known that pregnancy causes multiple changes in the coagulation system which may lead to a hypercoagulable state. For example, during pregnancy and post-partum, the risk of venous thrombosis is almost fivefold higher than in the non-pregnant state. In addition, clotting factors increase, natural inhibitors of coagulation decrease, changes occur in the fibrinolytic system, venous stasis increases, as well as increases in vascular injury at delivery from placental separation, cesarean section, or infection [Barbour, et al., *Obstet Gynecol* 86:621–633, 1995].

Although the risk of a complication due to this hypercoagulable state in women without any risk factors is small, women with a history of thromboembolic events are at an increased risk for recurrence when they become pregnant. In addition, women with underlying hypercoagulable states, including the recent discovery of hereditary resistance to activated protein C, also have a higher recurrence risk [Dahlback, *Blood* 85:607–614, 1995].

Therefore, it has been suggested that women with a history of venous thromboembolic events who are found to have a deficiency in antithrombin-III, protein C, or protein S, are at an appreciable risk of recurrent thrombosis and should be considered for prophylactic anticoagulant therapy [Conrad, et al., *Throm Haemost* 63:319–320, 1990].

The conditions of preeclampsia and eclampsia in pregnant women appear to be a state of increased coagulopathy as indicated by an increase in fibrin formation, activation of the fibrinolytic system, platelet activation and a decrease in platelet count [*Clin Obstet Gynecol* 35:338–350, 1992]. Preeclampsia is thought to be the result of uteroplacental ischemia due to an anomaly of the "vascular insertion" of the placenta. Consequences of preeclampsia include hypertension as well as DIC which leads to the release of numerous microthrombi which cause placental, renal, hepatic and cerebral lesions [*Rev Fr Gynecol Obstet* 86:158–163, 1991]. Furthermore, preeclampsia can lead to a severe and life threatening condition known as the HELLP syndrome which is defined as preeclampsia complicated by thrombocytopenia, hemolysis and disturbed liver function [Rathgeber, et al., *Anasth Intensivther Notfallmed* 25:206–211, 1990]. Additionally, it has been documented that there is a reduction in protein C levels in pregnant women with severe preeclampsia when compared to normal pregnancies [De Stefano, et al., *Thromb Haemost* 74:793–794, 1995].

Thus, the risk of venous thromboembolic complications occurring in pregnant women is a major concern, especially in women who have a history of thromboembolic events. Although the possibility of severe complications such as preeclampsia or DIC is relatively low, it has been suggested that it is essential to start therapy of DIC as soon as it has been diagnosed by onset of inhibition of the activated coagulation system [Rathgeber, et al., *Anasth Intensivther Notfallmed* 25:206–211, 1990]. The complications of preeclampsia or DIC is analogous to the situation that occurs in sepsis in that there is a hypercoagulable state and a decrease in the levels of protein C.

MAJOR SURGERY/TRAUMA

Patients recovering from major surgery or accident trauma frequently encounter blood coagulation complications as a result of an induced hypercoagulable state [Watkins, et al., *Klin Wochenschr* 63:1019–1027, 1985]. Hypercoagulable states are increasingly recognized as causes of venous thromboembolism in surgical patients [Thomas, et al., *Am J Surg.* 158:491–494, 1989; LeClerc, J. R., *Clin Appl Thrombosis/Hemostasis* 3(3):153–156, 1997]. Furthermore, this hypercoagulable state can lead to complications with DIC-like symptoms, which is infrequently encountered but, nonetheless, is devastating and often fatal when it occurs. [Collins, et al., *Am J Surg.* 124:375–380, 1977].

In addition, patients undergoing coronary artery bypass grafting (CABG) [Menges, et al., *J Cardiothor Vasc An.* 10:482–489, 1996], major spinal surgery [Mayer, et al., *Clin Orthop.* 245:83–89, 1989], major abdominal surgery [Blamey, et al., *Thromb Haemost.* 54:622–625, 1985], major orthopedic surgery or arthroplastic surgery of the lower extremities [LeClerc, 1997], or other types of surgery [Thomas, et al., *Am J Surg.* 158:491–494, 1989], occasionally develop venous thromboembolic complications. Additionally, investigators in Japan have proposed treating microvascular thrombosis associated with spinal cord injury [patent application JP8325161A] with plasma derived protein C at a dose of 1–10 mg/day for an adult, or preferably, 2–6 mg divided by 1–2 times to be administered as a bolus or by intravenous infusion.

It has been suggested that anticoagulant therapy is important as a prophylactic therapy to prevent venous thromboembolic events in major surgery or trauma patients [Thomas, et al., 1989; LeClerc, 1997]. For example, many patients who succumb from pulmonary embolism have no clinical evidence of preceding thromboembolic events and die before the diagnosis is made and the treatment is instituted [LeClerc, 1997]. Existing prophylactic methods e.g., warfarin, low molecular weight heparins, have limitations such as residual proximal thrombosis or the need for frequent dose adjustments.

ARDS

Adult respiratory distress syndrome [ARDS] is characterized by lung edema, microthrombi, inflammatory cell infiltration, and late fibrosis. Pivotal to these multiple cellular and inflammatory responses is the activation of coagulation resulting in a hypercoagulable state. Common ARDS-associated coagulation disorders include intravascular coagulation and inhibition of fibrinolysis. Fibrin formed by the activation of the coagulation system and inhibition of fibrinolysis presumably contributes to the pathogenesis of acute lung injury. Sepsis, trauma and other critical diseases are important risk factors that lead to ARDS [Hasegawa, et al., *Chest* 105(1):268–277, 1994].

ARDS is associated with an activation of coagulation and inhibition of fibrinolysis. Considerable clinical evidence exists for the presence of pulmonary vascular microemboli which is analogous to the hypercoagulation that is present in DIC. Therefore, a need currently exists for an effective treatment of this hypercoagulable state associated with ARDS.

For ease of comparison of the dose levels of protein C noted in literature and patent documents, Table I sets forth normalized dose levels of several studies in humans or non-human primates. These data establish dose levels that are higher or lower than the dose levels provided in the present invention. Significantly, the human studies were done utilizing plasma derived protein C zymogen while the non-human primate study utilized recombinant human aPC.

TABLE I

| REFERENCE | PUBLISHED DOSE | NORMALIZED DOSE* |
|---|---|---|
| Taylor, et al., U.S. Pat. No. 5,009,889 | IV administration of between 2 and 64 ug aPC/kg/minute; a bolus of between 1 and 10 mg aPC may be given additionally. [column 5, lines 14–19] | 120 ug/kg/hr to 3800 ug/kg/hr infused for 8 to 10 hours |
| Rivard, et al., J. Ped. 126:646, 1995 | IV administration at a close of 100 IU*/kg plasma derived protein C zymogen during a 15 to 20 minute period every 6 hours during the acute phase and then 1 to 2 times a day for 9 days. [p. 648, column 1, 1$^{st}$ paragraph] | 400 ug/kg in 15 to 20 minutes |
| Gerson, et al., Ped. 91:418–422, 1993 | IV administration at a bolus dose of 70 IU*/kg plasma derived protein C zymogen every 6 hours subsequently, continuous infusion of 10 IU/kg/hr for 11 days was given. [p. 419, column 2, 1$^{st}$ paragraph] | 280 ug/kg bolus every 6 hours, then continuous infusion of 40 ug/kg/hr for 11 days |
| Rintala, et al., Lancet 347:1767, 1996 | IV administration was started 3 hours after admission and continued for 7 days. 100 IU*/kg plasma derived protein C zymogen every 6 hours and later adjusting dose to plasma protein C activity. [p. 1767, column 2, 2$^{nd}$ paragraph] | 400 ug/kg bolus every 6 for 7 days |
| Smith, et al., Thromb. Haem., PS-1709, 1997 | Each patient had a loading dose of 100 IU*/kg plasma derived protein C zymogen followed by a continuous infusion of 15 IU/kg. [p. 419, column 1, PS-1709] | 400 ug/kg bolus + 60 ug/kg/hr (no infusion time was given) |
| Fujiwara, et al., Japanese Pat. JP7097335A | The usual dose is 20–1000 U** plasma derived APC/kg body weight/day, or more preferably 50–300 U/kg with divided administration of 1–2 times. As the method of administration, it is most appropriate to use intravenous infusion. [p. 9, paragraph 0016] | 4 ug/kg to 200 ug/kg. An infusion time was not given. |
| Okajima, et al., Japanese Pat. JP 8325161A | The effective dose of plasma derived PC or APC is 1–10 mg/day for an adult, or preferably 2–6 mg to be administered divided 1–2 times. As the method of administration, one can use bolus administration (in a single administration) or intravenous infusion. [p. 10, paragraph 0013] | 42 ug/hr to 420 ug/hr |
| Okajima, et al., Amer. J of Hematology, 33:277–278 (1990) | Administration of plasma derived APC (3 mg/day for 2 days, followed by 6 mg/day for 3 days). [p. 278, column 1, 1$^{st}$ full paragraph] | 2 ug/kg/hr and 4 ug/kg/hr. |
| Bang, et al., US Pat. 4,775,624 | The dose of activated protein L ranges from 1–10 mg as a loading dose followed by a continuous infusion in amounts ranging from 3–30 mg/day. [column 19, lines 55–59] | 1.8 to 18 ug/kg/hr An infusion time was not given. |

+ the normalized dose is a conversion of the reported dose to the equivalent ug/kg/hr designation.
*1 IU is equivalent to approximately 4 ug of PC
**1 U is defined as the amount which doubles the activated prothrombin time (APTT) in normal human plasma. This converts to approximately 5 Units /ug APC.

Despite these reports, however, the dosing regime for safe and efficacious therapy in humans suffering from an acquired hypercoagulable state or acquired protein C deficiency associated with sepsis, transplantations, burns, pregnancy, major surgery, trauma, or ARDS, remains unknown. These studies are not predictive of the use of recombinant activated protein C of the present invention in the treatment of hypercoagulable states or acquired protein C deficiency in humans.

The present invention discloses the use of aPC in a clinical trial in severe sepsis patients. In these patients, the r-aPC treated group demonstrated statistical improvement in organ functions, lowering of DIC markers and decrease in mortality as compared to the placebo control group. The doses of aPC used in the severe sepsis patients were 12, 18, 24, and 30 µg/kg/hr in a 48 hour infusion. The doses of 12 and 18 µg/kg/hr were not effective in this study. Surprisingly, the doses of 24 and 30 µg/kg/hr used in this study were efficacious and are considerably and unexpectedly low as compared to published pre-clinical pharmacology data.

In addition, the applicants have found that pre-clinical toxicology studies in non-human primates indicate the safety of aPC for a 96 hour infusion is limited to a top dose of around 50 µg/kg/hr. These data are also unexpected when compared to the prior art. In fact, the dose levels of r-aPC for humans that have been based on previous pre-clinical and clinical studies will be above the toxicological range established in the above toxicological studies.

SUMMARY OF THE INVENTION

The present invention provides a method of treating human patients with an acquired hypercoagulable state or acquired protein C deficiency which comprises administering to said patient by continuous infusion for about 24 to about 144 hours a dosage of about 20 μg/kg/hr to about 50 μg/kg/hr of activated protein C.

The invention further provides a method of treating human patients with an acquired hypercoagulable state or acquired protein C deficiency which comprises administering to said patient an effective amount of activated protein C to achieve activated protean C plasma levels in the range of 2 ng/ml to 200 ng/ml.

Thus, the present invention establishes methods utilizing aPC in the treatment of the hypercoagulable state or protein C deficiency associated with sepsis, purpura fulminans, and meningococcemia in human patients.

The present invention establishes methods utilizing aPC to treat the hypercoagulable state or protein C deficiency associated with severe burns.

The present invention establishes methods utilizing aPC to treat the hypercoagulable state or protein C deficiency associated with bone marrow and other organ transplantations.

The present invention establishes methods utilizing aPC to treat the hypercoagulable state or protein C deficiency associated with human patients undergoing or recovering from major surgery or severe trauma.

The present invention establishes methods utilizing aPC to treat the hypercoagulable state or protein C deficiency associated with complications during pregnancy.

The invention further provides a method of treating human patients with an acquired hypercoagulable state or acquired protein C deficiency associated with ARDS.

DETAILED DESCRIPTION OF THE INVENTION

For purposes of the present invention, as disclosed and claimed herein, the following terms are as defined below.

aPC or activated protein C refers to recombinant activated protein C. aPC includes and is preferably human protein C although aPC may also include other species or derivatives having full protein C proteolytic, amidolytic, esterolytic, and biological (anticoagulant or pro-fibrinolytic) activities. Examples of protein C derivatives are described by Gerlitz, et al., U.S. Pat. No. 5,453,373, and Foster, et al., U.S. Pat. No. 5,516,650, the entire teachings of which are hereby incorporated by reference. Recombinant activated protein C may be produced by activating recombinant human protein C zymogen in vitro or by direct secretion of the activated form of protein C. Protein C may be produced in cells, eukaryotic cells, transgenic animals, or transgenic plants, including, for example, secretion from human kidney 293 cells as a zymogen then purified and activated by techniques known to the skilled artisan.

Treating—describes the management and care of a patient for the purpose of combating a disease, condition, or disorder and includes the administration of aPC prophylactically to prevent the onset of the symptoms or complications of the disease, condition, or disorder. or administering aPC to eliminate the disease, condition, or disorder.

Continuous infusion—continuing substantially uninterrupted the introduction of a solution into a vein for a specified period of time.

Bolus injection—the injection of a drug in a defined quantity (called a bolus) over a period of time up to about 120 minutes.

Suitable for administration—a lyophilized formulation or solution that is appropriate to be given as a therapeutic agent.

Receptacle—a container such as a vial or bottle that is used to receive the designated material, i.e., aPC Unit dosage form—refers to physically discrete units suitable as unitary dosages for human subjects, each unit containing a predetermined quantity of active material calculated to produce the desired therapeutic effect, in association with a suitable pharmaceutical excipient.

Hypercoagulable states—excessive coagulability associated with disseminated intravascular coagulation, pre-thrombotic conditions, activation of coagulation, or congenital or acquired deficiency of clotting factors such as aPC.

Zymogen—Protein C zymogen, as used herein, refers to secreted, inactive forms, whether one chain or two chains, of protein C.

Juvenile—a human patient including but not restricted to newborns, infants, and children younger than 18 years of age.

Effective amount—a therapeutically efficacious amount of a pharmaceutical compound.

Purpura fulminans—ecchymotic skin lesions, fever, hypotension associated with bacterial sepsis, viral, bacterial or protozoan infections. Disseminated intravascular coagulation is usually present.

The present invention relates to the treatment or prevention of hypercoagulable states or acquired protein C deficiency associated with sepsis, transplantations, burns, pregnancy, major surgery, trauma, or ARDS, with activated protein C. The aPC can be made by techniques well known in the art utilizing eukaryotic cell lines, transgenic animals, or transgenic plants. Skilled artisans will readily understand that appropriate host eukaryotic cell lines include but are not limited to HEPG-2, LLC-MK$_2$, CHO-K1, 293, or AV12 cells, examples of which are described by Grinnell in U.S. Pat. No. 5,681,932, herein incorporated by reference. Furthermore, examples of transgenic production of recombinant proteins are described by Drohan, et al., in U.S. Pat. No. 5,589,604 and Archibald, et al., U.S. Pat. No. 5,650,503, herein incorporated by reference.

To be fully active and operable under the present methods, the aPC made by any of these methods must undergo post translational modifications such as the addition of nine gamma-carboxy-glutamates (gamma-carboxylation i.e. Gla content), the addition of one erythro-beta-hydroxy-Asp (beta-hydroxylation), the addition of four Asn-linked oligosaccharides (glycosylation), the removal of the leader sequence (42 amino acid residues) and removal of the dipeptide Lys 156-Arg 157. Without such post-translational modifications, aPC is not fully functional or is non-functional.

The aPC can be formulated according to known methods to prepare pharmaceutically useful compositions. The aPC will be administered parenterally to ensure its delivery into the bloodstream in an effective form by injecting the appropriate dose as continuous infusion for about 24 to about 144 hours. The amount of aPC administered will be from about 20 μg/kg/hr to about 50 μg/kg/hr. More preferably, the amount of aPC administered will be about 22 μg/kg/hr to about 40 μg/kg/hr. Even more preferably the amount of aPC administered will be about 22 μg/kg/hr to about 30 μg/kg/hr. The most preferable amounts of aPC administered will be about 24 μg/kg/hr or about 30 μg/kg/hr.

Alternatively, the aPC will be administered by injecting a portion (⅓ to ½) of the appropriate dose per hour as a bolus injection over a time from about 5 minutes to about 120 minutes, followed by continuous infusion of the appropriate dose for about twenty-three hours to about 144 hours which results in the appropriate dose administered over 24 hours to 144 hours.

Only after carefully controlled clinical studies and exhaustive experimental studies have the applicants discovered that the dose levels of about 20 µg/kg/hr to about 50 µg/kg/hr continually infused for about 24 hours to about 144 hours results in efficacious therapy. The most preferable dose level of aPC to be administered for treating human patients with an acquired hypercoagulable state or acquired protein C deficiency as described herein will be about 24 µg/kg/hr.

Preparation 1

Preparation of Human Protein C

Recombinant human protein C (r-hPC) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells was plasmid pLPC which is disclosed in Bang, et al., U.S. Pat. No. 4,992,373, the entire teaching of which is incorporated herein by reference. The construction of plasmid pLPC is also described in European Patent Publication No. 0 445 939, and in Grinnell, et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C was separated from the culture fluid by an adaptation of the techniques of Yan, U.S. Pat. No. 4,981,952, the entire teaching of which is herein incorporated by reference. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen was eluted with 20 mM Tris, 150 mM NaCl, 10 nuM CaCl2, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650 M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C was eluted with 20 mM Tris, pH 7.4.

The eluted protein was prepared for activation by removal of residual calcium. The recombinant human protein C was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 6.5. Following loading of the protein, the Chelex-100 column was washed with one column volume of the same buffer before disconnecting it from the series. The anion exchange column was washed with 3 column volumes of equilibration buffer before eluting the protein with 0.4 M NaCl, 20 mM Tris-acetate, pH 6.5. Protein concentrations of recombinant human protein C and recombinant activated protein C solutions were measured by UV 280 nm extinction $E^{0.1\%}$=1.85 or 1.95, respectively.

Preparation 2

Activation of Recombinant Human Protein C

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/ml resin. The thrombin solution was circulated through the column for approximately 3 hours before adding MEA to a concentration of 0.6 ml/l of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified r-hPC was made 5mM in EDTA (to chelate any residual calcium) and diluted to a concentration of 2 mg/ml with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the r-hPC and thrombin resin. The effluent was collected and immediately assayed for amidolytic activity. If the material did not have a specific activity (amidolytic) comparable to an established standard of aPC, it was recycled over the thrombin column to activate the r-hPC to completion. This was followed by 1:1 dilution of the material with 20 mM buffer as above, with a pH of anywhere between 7.4 or 6.0 (lower pH being preferable to prevent autodegradation) to keep the aPC at lower concentrations while it awaited the next processing step.

Removal of leached thrombin from the aPC material was accomplished by binding the aPC to an anion exchange resin (Fast Flow Q, Pharmacia) equilibrated in activation buffer (either 20 mM Tris, pH 7.4 or preferably 20 mM Tris-acetate, pH 6.5) with 150 mM NaCl. Thrombin passes through the column and elutes during a 2–6 column volume wash with 20 mM equilibration buffer. Bound aPC is eluted with a step gradient using 0.4 M NaCl in either 5 mM Tris-acetate, pH 6.5 or 20 mM Tris, pH 7.4. Higher volume washes of the column facilitated more complete removal of the dodecapeptide. The material eluted from this column was stored either in a frozen solution (−20° C.) or as a lyophilized powder.

The amidolytic activity (AU) of aPC was determined by release of p-nitroanaline from the synthetic substrate H-D-Phe-Pip-Arg-p-nitroanilide (S-2233) purchased from Kabi Vitrum using a Beckman DU-7400 diode array spectrophotometer. One unit of activated protein C was defined as the amount of enzyme required for the release of 1 µmol of p-nitroaniline in 1 min. at 25° C., pH 7.4, using an extinction coefficient for p-nitroaniline at 405 nm of 9620 $M^{-1}cm^{-1}$.

The anticoagulant activity of activated protein C was determined by measuring the prolongation of the clotting time in the activated partial thromboplastin time (APTT) clotting assay. A standard curve was prepared in dilution buffer (1 mg/ml radioimmunoassay grade BSA, 20 mM Tris, pH 7.4, 150 mM NaCl, 0.02% $NaN_3$) ranging in protein C concentration from 125–1000 ng/ml, while samples were prepared at several dilutions in this concentration range. To each sample cuvette, 50 μl of cold horse plasma and 50 μl of reconstituted activated partial thromboplastin time reagent (APTT Reagent, Sigma) were added and incubated at 37° C. for 5 min. After incubation, 50 μl of the appropriate samples or standards were added to each cuvette. Dilution buffer was used in place of sample or standard to determine basal clotting time. The timer of the fibrometer (CoA Screener Hemostasis Analyzer, American Labor) was started upon the addition of 50 μl 37° C. 30 mM $CaCl_2$ to each sample or standard. Activated protein C concentration in samples are calculated from the linear regression equation of the standard curve. Clotting times reported here are the average of a minimum of three replicates, including standard curve samples.

The above descriptions enable one with appropriate skill in the art to prepare aPC and utilize it in the treatment of hypercoagulable states or acquired protein C deficiency associated with but not limited to sepsis, transplantations, burns, pregnancy, major surgery/trauma, and ARDS.

EXAMPLE 1

Human Plasma Levels of aPC

Six human patients received an i.v. infusion of aPC at 1 mg/m² /hour or about 0.024 mg/kg/hr over a 24 hour period. The aPC administered was a lyophilized formulation containing 10 mg aPC, 5 mM Tris acetate buffer and 100 mM sodium chloride reconstituted with two ml of water and adjusted to pH 6.5.

Plasma concentrations of aPC were measured using an Immunocapture-Amidolytic Assay. Blood was collected in the presence of citrate anticoagulant and benzamidine, a reversible inhibitor of aPC. The enzyme was captured from plasma by an aPC specific murine monoclonal antibody, C3, immobilized on a microtiter plate. The inhibitor was removed by washing and the amidolytic activity or aPC was measured using an oligopeptide chromogenic substrate. Following incubation for 16–20 h at 37° C., the absorbance was measured at 405 nm and data are analyzed by a weighted linear curve-fitting algorithm. aPC concentrations were estimated from a standard curve ranging in concentrations from 0–100 ng/ml. The limit of quantitation of the assay was 1.0 ng/ml. The aPC dose levels and plasma concentrations were measured at about 24 hours. The dose of 0.024 mg/kg/hr yields a plasma concentration of about 50 ng/ml at 24 hours.

EXAMPLE 2

Double-blinded Placebo-controlled Trial in Human Patients With Sepsis, Stage 1

This protocol is a two-stage, double-blinded placebo-controlled trial in patients with severe sepsis. In Stage 1, a total of 72 patients were infused for 48 hours with recombinant human activated protein C (r-aPC).

Entry criteria included three of the four commonly accepted criteria for sepsis (heart rate, respiratory effort, increased/decreased temperature, increase/decrease white blood cell count). The patients also had to demonstrate some degree of organ dysfunction defined as either shock, decreased urine output, or hypoxemia. Four different doses were utilized; 12, 18, 24, 30 μg/kg/hr. The r-aPC was infused for 48 hours by a continuous infusion method. The primary endpoints of this study were: safety as a function of dose and dose duration, and; the ability of r-aPC to correct coagulopathy as a function of dose and dose duration.

Mortality information includes all doses, even the lowest doses, unless otherwise specified. It is important to note that our placebo mortality is consistent with anticipated placebo mortality. A 28 day all cause mortality was the end-point in patients receiving placebo vs. patients receiving r-aPC.

The overall observed placebo mortality rate was 38% (10/26) and the overall observed r-aPC mortality rate was 20% (9/46). A subgroup involving only the top two doses of r-aPC (24 and 30 μg/kg/hr) vs placebo patients had an observed mortality rate of 13% (3/24).

A second subgroup analysis included patients with an acquired protein C deficiency, defined as a baseline protein C activity of less that; 60%. Of the 64 patients that have baseline protein C activity data available, 61 patients or 95%, had an acquired protein C deficiency at the time of entry into the study. The observed placebo mortality rate for protein C deficient patients was 41% (9/22) and the observed r-aPC mortality rate for protein C deficient patients was 18% (7/39).

A significant piece of information suggesting that low dose treatment with r-aPC is of benefit with patients with severe sepsis includes the mean time to death in placebo patients vs. treated patients. Of the ten patients who died in the placebo group, the mean time to death was 6 days. In the r-aPC treated patients, the mean time to death was 14 days. Additionally, 4 of the 9 patients who died in the r-aPC treatment arm survived 21 or more days and subsequently succumbed to an event unrelated to their first episode of sepsis. Two of the four late deaths occurred in the low dose group (12 μg/kg/hr). Both of these patients remained in the ICU and mechanically ventilated the entire duration of the study until their death (day 27). The other two patients with late deaths were in the high dose group (30 ug/kg/hr). Both of these patients showed initial improvement. Within two weeks both were off mechanical ventilation and transferred from the ICU. One patient died a week later from sepsis induced respiratory distress after requesting a "do not resuscitate" (DNR) order inacted. The second patient died on day 28 after suffering an episode of pulmonary insufficiency related to a second episode of sepsis. This patient had also requested DNR status and therefore was not reintubated. It should be noted that retreatment with r-aPC of patients that develop a second episode of severe sepsis during the 28 day study was not approved under the treatment protocol.

The mortality information in this study is surprising and unexpected. No other double-blinded, placebo controlled sepsis study has generated data demonstrating such a marked reduction in 28-day all cause mortality.

EXAMPLE 3

Formulation of Activated Protein C

A stable lyophilized formulation of activated protein C was prepared by a process which comprises lyophilizing a solution comprising about 2.5 mg/mL activated protein C, about 15 mg/mL sucrose, about 20 mg/mL NaCl, and a sodium citrate buffer having a pH greater than 5.5 but less than 6.5. Additionally, the stable lyophilized formulation of activated protein C comprises lyophilizing a solution comprising about 5 mg/mL activated protein C, about 30 mg/mL sucrose, about 38 mg/mL NaCl, and a citrate buffer having a pH greater than 5.5 but less than 6.5.

The ratio of aPC:salt:bulking agent (w:w:w) is an important factor in a formulation suitable for the freeze drying process. The ratio varies depending on the concentration of aPC, salt selection and concentration and bulking agent selection and concentration. Particularly, a ratio of about 1 part activated protein C to about 7.6 parts salt to about 6 parts bulking agent is preferred.

A unit dosage formulation of activated protein C suitable for administration by continuous infusion was prepared by mixing activated protein C, NaCl, sucrose, and sodium citrate buffer. After mixing, 4 mL of the solution was transferred to a unit dosage receptacle and lyophilized. The unit dosage receptacle containing about 5 mg to about 20 mg of activated protein C, suitable for administering a dosage of about 0.02 mg/kg/hr to about 0.05 mg/kg/hr to patients in need thereof, was sealed and stored until use.

What is claimed is:

1. A method of treating a patient with an acquired hypercoagulable state or acquired protein C deficiency which comprises administering to said patient by continuous infusion for about 24 to about 144 hours a dosage of about 22 $\mu$g/kg/hr to about 40 $\mu$g/kg/hr of human activated protein C.

2. The method of claim 1 wherein the dosage is about 22 $\mu$g/kg/hr to about 30 $\mu$g/kg/hr of human activated protein C.

3. The method of claim 1 wherein the dosage is about 30 $\mu$g/kg/hr of human activated protein C.

4. The method of claim 1 wherein the dosage is about 24 $\mu$g/kg/hr of human activated protein C.

5. The method according to claim 1 wherein said hypercoagulable state or protein C deficiency is associated with sepsis.

6. The method according to claim 2 wherein said hypercoagulable state or protein C deficiency is associated with sepsis.

7. The method according to claim 3 wherein said hypercoagulable state or protein C deficiency is associated with sepsis.

8. The method according to claim 4 wherein said hypercoagulable state or protein C deficiency is associated with sepsis.

9. The method according to claim 1 wherein said hypercoagulable state or protein C deficiency is associated with purpura fulminans.

10. The method according to claim 2 wherein said hypercoagulable state or protein C deficiency is associated with purpura fulminans.

11. The method according to claim 3 wherein said hypercoagulable state or protein C deficiency is associated with purpura fulminans.

12. The method according to claim 4 wherein said hypercoagulable state or protein C deficiency is associated with purpura fulminans.

13. The method according to claim 1 wherein said hypercoagulable state or protein C deficiency is associated with meningococcemia.

14. The method according to claim 2 wherein said hypercoagulable state or protein C deficiency is associated with meningococcemia.

15. The method according to claim 3 wherein said hypercoagulable state or protein C deficiency is associated with meningococcemia.

16. The method according to claim 4 wherein said hypercoagulable state or protein C deficiency is associated with meningococcemia.

17. The method according to claim 1 wherein said human patient is a juvenile.

18. The method according to claim 1 wherein said hypercoagulable state or protein C deficiency is associated with burns.

19. The method according to claim 1 wherein said method of treating is for humans suffering from venous thromboembolic complications associated with bone marrow and other organ transplantation.

20. The method according to claim 1 wherein said method of treating is for humans suffering from venous thromboembolic complications associated with surgery or trauma.

21. The method according to claim 1 wherein said method of treatment is for humans suffering with an acquired hypercoagulable state or protein C deficiency associated with complications during pregnancy.

22. The method according to claim 2 wherein said hypercoagulable state or protein C deficiency is associated with acquired hypercoagulable state or protein C deficiency associated with complications during pregnancy.

23. The method according to claim 1 wherein said hypercoagulable state or protein C deficiency is associated with ARDS.

24. The method according to claim 2 wherein said hypercoagulable state or protein C deficiency is associated with ARDS.

25. The method according to claim 3 wherein said hypercoagulable state or protein C deficiency is associated with ARDS.

26. The method according to claim 4 wherein said hypercoagulable state or protein C deficiency is associated with ARDS.

27. The method of claim 1 wherein a bolus injection of human activated protein C is followed by said continuous infusion.

28. The method of claim 2 wherein a bolus injection of human activated protein C is followed by said continuous infusion.

29. The method of claim 3 wherein a bolus injection of human activated protein C is followed by said continuous infusion.

30. The method of claim 4 wherein a bolus injection of human activated protein C is followed by said continuous infusion.

* * * * *